United States Patent [19]

Chan

[11] 4,182,862

[45] Jan. 8, 1980

[54] PROCESS FOR THE PREPARATION OF 1,3-DISUBSTITUTED-2-AZOYL-2-PROPEN-1-ONES

[75] Inventor: Hak-Foon Chan, Doylestown, Pa.

[73] Assignee: Rohm and Haas Company, Philadelphia, Pa.

[21] Appl. No.: 952,435

[22] Filed: Oct. 18, 1978

[51] Int. Cl.$^2$ ............... C07D 233/60; C07D 401/06; C07D 405/06; C07D 409/06
[52] U.S. Cl. .................... 542/440; 548/262; 542/432; 542/436; 542/453; 542/458; 548/336; 548/341
[58] Field of Search ............... 548/341, 336; 260/308 R; 542/432, 436, 438, 453, 458, 440

[56] References Cited

U.S. PATENT DOCUMENTS

| | | | |
|---|---|---|---|
| 3,575,999 | 4/1971 | Godefroi et al. | 548/336 |
| 3,681,375 | 8/1972 | Adolphi et al. | 548/341 |
| 3,723,453 | 3/1973 | Gradnik et al. | 548/336 |
| 3,872,117 | 3/1975 | Meiser et al. | 548/336 |
| 3,926,999 | 12/1975 | Poetsch | 542/440 |
| 4,067,989 | 1/1978 | Shephard et al. | 542/458 |

OTHER PUBLICATIONS

Fieser et al., Organic Chemistry, 3rd Ed., pp. 57–59, N.Y., Reinhold, 1956.

*Primary Examiner*—Natalie Trousof

[57] ABSTRACT

This invention involves an improved process for the preparation of pesticidal 1,3-disubstituted-2-azoyl-2-propen-1-ones from the corresponding dibromoketones and azoles at a temperature from about 60° C. to 180° C. either neat or in the presence of an inert solvent.

6 Claims, No Drawings

PROCESS FOR THE PREPARATION OF 1,3-DISUBSTITUTED-2-AZOYL-2-PROPEN-1-ONES

SUMMARY OF THE INVENTION

This invention relates to an improved process for the preparation of 1,3-disubstituted 2-azoyl-2-propen-1-ones of the formula

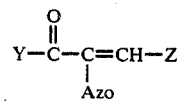  (I)

wherein Y and Z are independently an alkyl group, an aryl group, a substituted aryl group, a pyridyl group, a substituted pyridyl group, a furyl group, a substituted furyl group, a thienyl group, or a substituted thienyl group and azo is a group of the formula

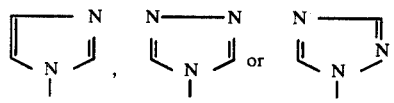

which are useful as pesticidal agents and in particular are useful in the control of phytopathogenic fungi. The improved process of this invention involves the bromination of a 1,3-disubstituted 2-propen-1-one of formula (II)

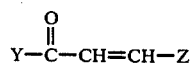  (II)

to give a dibromoketone of formula (III)

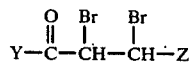  (III)

which is then reacted with a group of the formula

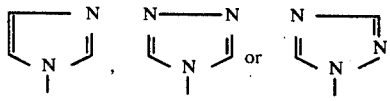

to give, via the simultaneous addition of an imidazole or triazole group and the dehydrohalogenation of the dibromoketone structure, the product of formula (I).

BACKGROUND OF THE INVENTION

It is reported in the literature that compounds of the general formula (I) are useful in the control of phytopathogenic fungi on agronomic crops. The South African Patent Application No. 765,920 published Sept. 28, 1976 assigned to Imperial Chemical Industries Ltd. discloses this general class of compounds and their use in controlling fungi. This specification discloses two procedures for the preparation of these compounds. In both procedures the imidazole or triazole ring is added onto the aryl alkyl ketone moiety in the initial steps of the reaction sequence. Both imidazole and triazole are expensive reagents and the addition of these compounds in the initial steps of a reaction sequence adds considerably to the overall cost of the final product since the loss in yield of each additional step in the reaction sequence adds significantly to the cost of the final product. Moreover, the dibromoketone of formula (III), can be prepared in simple reaction sequences in high yields starting with inexpensive raw materials.

DETAILED DESCRIPTION OF THE PRESENT INVENTION

The improved process of the present invention relates to the preparation of compounds of the formula

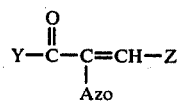  (I)

wherein Y and Z are independently selected from the group consisting of ($C_1$-$C_{12}$) alkyl, phenyl, pyridyl, furyl or thienyl or phenyl, pyridyl, furyl or thienyl, preferably phenyl substituted with up to three substituents, preferably with up to two substituents, selected from the group consisting of halogen, nitro, cyano, ($C_1$-$C_4$)alkoxy or ($C_1$-$C_4$)alkyl; and Azo is a group of the formula

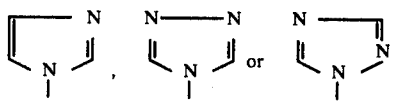

The improved process comprises reacting a dibromoketone of the formula

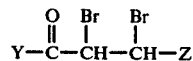  (III)

wherein Y and Z are as defined above, with a heterocyclic compound of the formula Azo-H  (iv)

wherein the group Azo is as defined above, at temperatures from about 60° C. to about 180° C. either neat or in the presence of an inert solvent. Typical inert solvents which can be utilized in the process of the present invention include dipolar aprotic solvents such as dimethylsulfoxide, N,N-dimethylformamide, tetrahydrofuran, dioxane and the like.

The reaction mixture is then stripped of its solvent if one is utilized, diluted with water and extracted with an appropriate solvent such as carbon tetrachloride, chloroform, dichloromethane, methylene chloride and the like. This solvent solution is dried over an appropriate drying agent such as magnesium sulfate, sodium sulfate and the like. This solution can then be evaporated to dryness to obtain the free base or treated with an equivalent or excess amount of a mineral acid such as halogen, sulfuric, phosphoric or nitric acid to give the mineral acid salt. If the salt does not readily precipitate from the solvent, a suitable anhydrous solvent such as diethylether can be added to force it out of solution or it can be stripped to dryness.

The following examples are provided merely to illustrate the process of the present invention and are not to be construed in any manner, as limiting the scope of this invention.

EXAMPLE I

1. Process for the preparation of 2-(N-imidazoly)-1-(2-nitrophenyl)-3-(2,4-dichlorophenyl)-2-propen-1-one HCl A. 1-(2-nitrophenyl)-3-(2,4-dichlorophenyl)-2propen-1-one To a solution of 10.6 g (0.06 mole) of 2,4-dichlorobenzaldehyde, 10 g (0.06 mole) of 2-nitroacetophenone in 75 ml of methanol is added an aqueous solution containing 3.5 g (0.065 mole) of potassium hydroxide in one portion with stirring. The reaction temperature is kept under room temperature with an ice bath. Yellow precipitates form immediately and are collected by filtration. The solids are washed with cold methanol and then dried in a vacuum oven to give 17 g of desired product, mp 130°-2°.

B. 2,3-Dibromo-1-(2-nitrophenyl)-3-(2,4-dichlorophenyl)propan-1-one

To a solution of 10 g (0.03 mole) of 1-(2-nitrophenyl)-3-(2,4-dichlorophenyl)-2-propen-1-one in 50 ml of methylene chloride is added 5.6 g (0.035 mole) of bromine dropwise at room temperature. Reaction mixture is stirred overnight. Solvent is then evaporated under vacuum to give a pale yellow solid which is triturated with cold ethanol to give 13 g of product, mp 176°-7°.

,4-dichlorophenyl)-2-propen-1-one HCl nyl)-3-(2

A mixture of 5 g (0.01 m) of 2,3-dibromo-1-(2-nitrophenyl)-3-(2,4-dichlorophenyl) propan-1-one and 3 g (0.01 mole) of imidazole is heated at 150° overnight. Reaction mixture is diluted with water and extracted with methylene chloride. The combined methylene chloride extracts are dried over MgSO$_4$. Drying agent is filtered and dry hydrogen chloride gas is bubbled through the solution until it is strongly acidic. Anhydrous ether is added to the methylene chloride solution and the precipitate is collected by filtration and dried to give the desired product, mp 215 (dec.).

Anal. for C$_{18}$H$_{12}$Cl$_3$N$_3$O$_3$: Calc'd. (found), C, 50.91(50.36), H, 2.85 (2.83); Cl, 25.04 (23.38); N, 9.89 (10.50); O, 11.30 (10.65).

EXAMPLE II

2. Process for Preparation of 2-[1-(1,2, 4-triazoyl)]-1-(2-nitrophenyl)-3-(2,4-dichlorophenyl)-2-propen-1-one. HCl A mixture of 5 g of 2,3-dibromo-1-(2-nitrophenyl)-3-(2,4-dichlorophenyl)-propan-1-one and 4 g of 1H-1,2,4-triazole is heated at 130° for 4 hours. The reaction mixture is poured into water and extracted with methylene chloride. The combined methylene chloride extracts are dried over MgSO$_4$. Drying agent is filtered and dry hydrogen chloride gas is bubbled through the solution until it is acidic. Anhydrous ether is added to the methylene chloride solution and the precipitate is collected by filtration and dried to give the desired product, mp 121°-3°.

Anal. for C$_{17}$H$_{11}$Cl$_3$N$_4$O$_3$: Calc'd. (found), C, 47.97 (47.18), H, 2.60 (2.53); Cl, 24.99 (23.28); N, 13.16 (12.77); O, 11.28 (11.19).

I claim:

1. In the process for the preparation of compounds of the formula

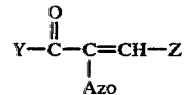

wherein Y and Z are independently selected from (C$_1$-C$_{12}$)alkyl, phenyl, pyridyl, furyl or thienyl or phenyl, pyridyl, furyl or thienyl substituted with up to three substituents selected from the group consisting of halogen, nitro, cyano, (C$_1$-C$_4$)alkoxy or (C$_1$-C$_4$)alkyl; and Azo is a group of the formula

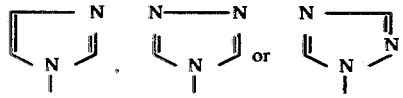

the improvement which comprises reacting a dibromoketone of the formula

wherein Y and Z are defined as above with a heterocyclic compound of the formula Azo-H wherein Azo is as defined above, at temperature from about 60° C. to about 180° C. either neat or in the presence of an inert solvent.

2. A process according to claim 1 wherein the reaction is carried out neat.

3. A process according to claim 2 which comprise the steps of treating the resultant free base with a mineral acid to obtain an acid salt.

4. A process according to claim 3 wherein Azo is an unsubstituted imidazole group.

5. A process according to claim 4 wherein Y and Z are independently a phenyl group or a phenyl group substituted with up to two substituents selected from halogen, nitro or cyano.

6. A process according to claim 5 wherein Y is phenyl, nitrophenyl or chlorophenyl and Z is phenyl, mono- or di-chlorophenyl, fluorophenyl, cyanophenyl or nitrophenyl.

* * * * *